(12) United States Patent
Harris

(10) Patent No.: US 6,623,959 B2
(45) Date of Patent: Sep. 23, 2003

(54) DEVICES AND METHODS FOR CELL HARVESTING

(75) Inventor: Ian Ross Harris, Belle Mead, NJ (US)

(73) Assignee: Ethicon, Inc., Somerville, NJ (US)

(*) Notice: Subject to any disclaimer, the term of this patent is extended or adjusted under 35 U.S.C. 154(b) by 1 day.

(21) Appl. No.: 09/880,118

(22) Filed: Jun. 13, 2001

(65) Prior Publication Data
US 2002/0192805 A1 Dec. 19, 2002

(51) Int. Cl.[7] .............................. C12N 5/00; C12M 1/12
(52) U.S. Cl. ...................... 435/325; 435/410; 435/261; 435/297.1; 435/308.1; 435/810; 210/446; 210/448
(58) Field of Search ................................ 435/261, 325, 435/410, 297.1, 308.1, 810; 210/787, 800, 446, 448

(56) References Cited

U.S. PATENT DOCUMENTS

| | | |
|---|---|---|
| 1,722,396 A | 7/1929 | Reiber |
| 3,190,546 A | 6/1965 | Raccuglia et al. |
| 3,420,437 A | 1/1969 | Blum et al. |
| 3,586,484 A | 6/1971 | Anderson |
| 3,642,163 A | 2/1972 | McFarland |
| 3,712,535 A | 1/1973 | Genese et al. |
| 3,722,789 A | 3/1973 | Kennedy |
| 3,774,455 A | 11/1973 | Seidler et al. |
| 3,851,817 A | 12/1974 | Buck |
| 3,859,671 A | 1/1975 | Tomasello |
| 3,877,634 A | 4/1975 | Rohde et al. |
| 3,951,334 A | 4/1976 | Fleming et al. |
| 3,953,172 A | 4/1976 | Shapiro et al. |

(List continued on next page.)

FOREIGN PATENT DOCUMENTS

| | | |
|---|---|---|
| CA | 461698 | 12/1979 |
| EP | 0 399 340 B1 | 11/1990 |
| EP | 0 444 270 A1 | 9/1991 |
| EP | 0 446 450 B1 | 9/1991 |
| EP | 0 512 769 A2 | 11/1992 |
| EP | 0 987 034 A3 | 3/2000 |
| EP | 0 987 034 A2 | 3/2000 |
| WO | WO 9013261 | 11/1990 |
| WO | WO 9317774 | 9/1993 |
| WO | WO 9416099 | 7/1994 |
| WO | WO 9423743 | 10/1994 |
| WO | WO 9501419 | 1/1995 |
| WO | WO 9601641 | 1/1996 |
| WO | WO 9639979 | 12/1996 |

OTHER PUBLICATIONS

Abstract, JP 11290060A, Date: Oct. 26, 1999; Applicant No. JP98108460, Date: Apr. 06, 1998.
Abstract, JP 7265407, Date: Oct. 17, 1995; Applicant No: JP 9482279, Date: Mar. 29, 1994.
Abstract JP 7136508, Date: May 30, 1995; Applicant No: JP 93288543, Date: Nov. 17, 1993.
Abstract SU 1500270, Date: Aug. 15, 1985; Applicant No: SU 4252848, Date: May 29, 1987.
Abstract FR 2696754, Date: Apr. 15, 1994; Applicant No: FR 9212554, Date: Oct. 14, 1992.
Abstract: WO 9601641 A.

Primary Examiner—David A. Redding
(74) Attorney, Agent, or Firm—Theodore J. Shatynski

(57) ABSTRACT

Devices and methods for cell harvesting are disclosed. More particularly this invention relates to devices and methods for enabling the formation of a dispersion of cells from tissue for medical or research use. This invention provides a rapid method for cell isolation thereby reducing the time and costs associated with the production of autologous cells where required, for example, for tissue engineering in the operating theater or in research. Alternately this invention may be used to separate a cell dispersion containing cells of varying sizes or types from a predigested tissue dispersion. Also a kit is disclosed which provides the basic components of the device and instructions on how to accomplish the use of the device.

22 Claims, 7 Drawing Sheets

U.S. PATENT DOCUMENTS

| | | |
|---|---|---|
| 4,026,433 A | 5/1977 | Crippa |
| 4,066,407 A | 1/1978 | Lupica |
| 4,150,089 A | 4/1979 | Linet |
| 4,285,463 A | 8/1981 | Intengan |
| 4,294,372 A | 10/1981 | Onishi |
| 4,431,423 A | 2/1984 | Weyant, Jr. |
| 4,587,018 A * | 5/1986 | Blomback et al. .......... 210/484 |
| 4,714,457 A | 12/1987 | Alterbaum |
| 4,834,703 A | 5/1989 | Dubrul et al. |
| 4,932,546 A | 6/1990 | Stannard |
| 5,045,047 A | 9/1991 | Hutchins et al. |
| 5,047,004 A | 9/1991 | Wells |
| 5,178,602 A | 1/1993 | Wells |
| 5,209,776 A | 5/1993 | Bass et al. |
| 5,292,362 A | 3/1994 | Bass et al. |
| 5,318,524 A | 6/1994 | Morse et al. |
| 5,409,833 A | 4/1995 | Hu et al. |
| 5,447,245 A | 9/1995 | Merhar |
| 5,503,284 A | 4/1996 | Li |
| 5,707,331 A | 1/1998 | Wells et al. |
| 5,833,927 A * | 11/1998 | Raybuck et al. ............ 422/101 |
| 5,888,409 A | 3/1999 | Morsiani et al. |
| 5,968,356 A | 10/1999 | Morsiani et al. |
| 6,139,757 A * | 10/2000 | Ohmura et al. ............. 210/797 |
| 6,197,579 B1 * | 3/2001 | Van Vlasselaer et al. ... 435/325 |

* cited by examiner

DEVICES AND METHODS FOR CELL HARVESTING

BACKGROUND OF THE INVENTION

1. Field of the Invention

This invention is concerned with devices and methods for harvesting cells. More particularly one embodiment of this invention relates to a device and a method for enabling the direct dispersion of cells from tissue for medical or research use.

2. Related Art

Advances in medical science and medical therapies have spurred the need for methods and apparatuses for isolating and collecting living cells for later use in medical or research procedures. Such procedures include seeding of the isolated cells to enhance grafting of tissue such as with burn victims and insertion of cells as a specific cell therapy to assist or augment the functioning of the recipient's own diseased or injured tissue or organs such as the liver.

Among the numerous methods and devices disclosed for isolating living cells are those disclosed in EP Pat. No. 446 450 B1. This patent discloses a device for digesting and processing tissue to produce endothelial cell products. One embodiment disclosed consists of a system of five primary subsystems: 1) fat collection unit (see FIG. 1); 2) digestion unit (see FIG. 2); 3) endothelial cell isolation unit (see FIG. 3); 4) vascular graft processing unit (see FIG. 4); and 5) endothelial cell deposition unit (see FIG. 4). An alternate embodiment (see FIG. 14) is disclosed consisting of a single vessel consisting of a vessel with three chambers: a digestion chamber (210), a waste chamber (212), and an isolation chamber (214). The digestion chamber (210) is separated from the waste chamber (212) by a plate (218) containing a normally closed check valve (220). A vent tube (222), containing a floating ball check valve (224), extends from the waste chamber (212) into the isolation chamber (214). The digestion chamber (210) communicates with the outside by means of a series of ports (228, 229, 230). The digestion chamber (210) is separated from the isolation chamber (214) by a screen (232). The isolation chamber (214) possesses two ports (234 and 236), each of which contains a two position valve (238 and 240). The first position allows communication between the middle of the ampoule (235) and the upper and lower portions of the ampoule. The second position allows communication between the middle of the ampoule (235) and the outside ports (234 and 236). Initially, both ampoule valves (238 and 240) are in the first position. The device is used as a catch-trap in line with a liposuction vacuum line connected to ports (228 and 230). After fat is collected, the liposuction lines are disconnected, ports 228 and 230 are capped and rinse solution (Media 199E, Hanks, saline, PBS, or other physiological buffered solution) is introduced through port (229). The fat is agitated in the rinse solution by any external means such as shaking. The device is then placed in a centrifuge, ampoule side up, and spun until the normally closed check valve (220) opens and the rinse solution drains into the waste chamber (212). The ball valve (224) in the vent tube (222) opens during this centrifugation step allowing the waste chamber (212) to vent air which is displaced by rinse solution. Digestion enzyme solution (collagenase, dispase, trypsin, or other tissue dissociation enzyme) is then introduced through port (229), again followed by agitation. When digestion is complete, the device is again centrifuged, ampoule side down. In order to isolate the endothelial cells which have separated into the ampoule (235), both valves (238 and 240) are turned to their second positions. The cell "pellet" may then be flushed out by attaching a pressure line to one of the ampoule ports (234 or 236).

U.S. Pat. No. 5,409,833 also discloses a single device for use in receiving, cleansing, digesting and isolating certain identifiable cells from tissues wherein the device comprises a housing defining a process chamber which includes a lower conical portion and a screen basket including a conical portion defining a lower part of the screen basket. The screen basket and its conical portion is positioned within the process chamber where the basket's lower conical portion defines a gap separating the screen basket from the housing with the size of the gap being substantially consistent across the screen basket and its conical portion. In use, the device requires several rinsing stages, a cell digestion stage, involving use of valving to produce, after centrifugation, a cell "pellet" of microvessel cells. This pellet is required to be removed introducing of a sterile buffered liquid through a port upstream of the "pellet" which forces the "pellet" through a second port which exits the device. The ports are required to be opened and closed by valves. Due to the intricacies of the device, it would be expected that reuse of the device in subsequent procedures would require thorough sterilization which could become hampered due to the intricacies of the passages and valving in the device.

While the foregoing patents disclose embodiments of cell separation devices as single apparatuses, it appears that operation may be cumbersome with the operator having to be intimately familiar with all the functions of the ports and valving for the various connections thereto. Additionally, reuse of these devices would appear to require thorough sterilization and cleaning procedures due to the complexity of the devices' passageways to insure sterile reuse of the devices.

The present invention provides an advance over the prior art by providing a sterile device and method of isolating cells from tissue in a simplified and rapid procedure as hereinafter described. The device also does not require any valving which makes cleaning and sterilization for reuse simpler as the intricacies of the passages of the previously disclosed devices are not present. Alternately, the device of the present invention is ideally suited for disposal use, thereby eliminating the concern of cleaning and sterilization of used devices.

SUMMARY OF THE INVENTION

Figure 1:
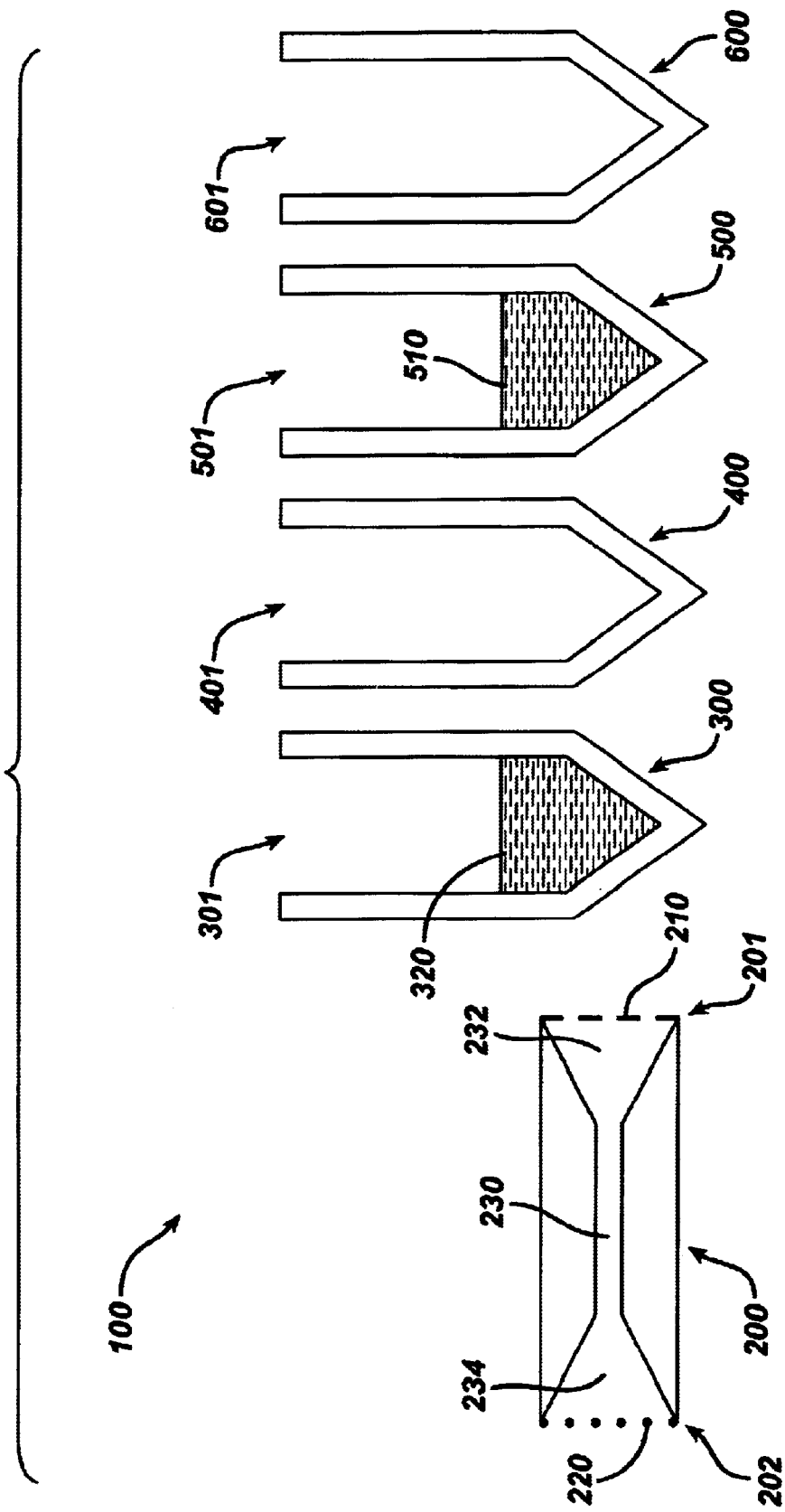
FIG. 1 depicts the basic unassembled components of one embodiment of the device of the invention.

One embodiment of this invention is directed to a device for separating cells from tissue comprising a housing defining a cell isolation unit having a first end and a second end, wherein the first end is adaptable for alternately receiving a tissue digestion chamber and a dispersed cell chamber and the second end is adaptable for alternately receiving a waste chamber and a serum chamber and the second end further containing a filter capable of filtering cells from a dispersion.

Another embodiment of the invention is directed to a method for isolating cells comprising the steps of:

a) providing a cell isolation unit having first and second open ends;

b) providing a source of tissue to form cells from tissue digested by a tissue degrading material in a tissue digestion chamber;

c) providing a waste chamber;

d) providing a source of serum in a serum chamber;

e) providing a cell dispersion chamber;

f) connecting the tissue digestion chamber to the first end of the cell isolation unit and the waste chamber to the second end of the cell isolation unit;

g) applying a force to cause the cells of the tissue digestion chamber to travel through the cell isolation unit thereby capturing the cells at the second end of the unit and allowing the other contents to pass through the cell isolation unit and into the waste chamber;

h) disconnecting the tissue digestion chamber and the waste chamber from the cell isolation unit;

i) connecting the cell dispersion chamber to the first end of the cell isolation unit and the serum chamber to the second end of the cell isolation unit; and j) applying a force to cause the contents of the serum chamber to pass through the cell isolation unit thereby washing the cells from the cell isolation unit into the dispersed cell chamber.

Alternate embodiments of the invention include a device for separating cells from tissue that may have already been digested or that may have already been dispersed and it is desirable to separate the cells from a dispersion or from a dispersion of various cells types and sizes. In such an embodiment the device comprises a housing defining a cell isolation unit having a first end and a second end, wherein the first end is adaptable for alternately receiving a first dispersed cell chamber and a second dispersed cell chamber and the second end is adaptable for alternately receiving a waste chamber and a serum chamber and the second end further containing a filter capable of filtering cells from a dispersion.

An alternate method according to this invention comprises a method for isolating cells comprising the steps of:

a) providing a cell isolation unit having first and second open ends;

b) providing a first dispersion of cells to be separated in a first cell dispersion chamber;

c) providing a waste chamber;

d) providing a source of serum in a serum chamber;

e) providing a second cell dispersion chamber;

f) connecting the first cell dispersion chamber to the first end of the cell isolation unit and the waste chamber to the second end of the cell isolation unit;

g) applying a force to cause the cells of the first cell dispersion chamber to travel through the cell isolation unit thereby capturing the cells at the second end of the unit and allowing the other contents to pass through the cell isolation unit and into the waste chamber;

h) disconnecting the first cell dispersion chamber and the waste chamber from the cell isolation unit;

i) connecting the second cell dispersion chamber to the first end of the cell isolation unit and the serum chamber to the second end of the cell isolation unit; and j) applying a force to cause the contents of the serum chamber to pass through the cell isolation unit thereby washing the cells from the cell isolation unit into the second cell dispersion chamber.

Yet another embodiment of the invention comprises a kit comprising a housing defining a cell isolation unit having a first end and a second end, wherein the first end is adaptable for alternately receiving a first dispersed cell chamber and a second dispersed cell chamber and the second end is adaptable for alternately receiving a waste chamber and a serum chamber and the second end further containing a filter capable of filtering cells from a dispersion with instructions of use comprising the steps of:

a) providing a first dispersion of cells to be separated in the first dispersed cell chamber;

b) connecting the first dispersed cell chamber to the first end of the cell isolation unit and the waste chamber to the second end of the cell isolation unit;

c) applying a force to cause the cells of the first dispersed cell chamber to travel through the cell isolation unit thereby capturing the cells at the second end of the unit and allowing the other contents to pass through the cell isolation unit and into the waste chamber;

d) disconnecting the first dispersed cell chamber and the waste chamber from the cell isolation unit;

e) connecting the second dispersed cell chamber to the first end of the cell isolation unit and the serum chamber containing a serum to the second end of the cell isolation unit; and f) applying a force to cause the contents of the serum chamber to pass through the cell isolation unit thereby washing the cells from the cell isolation unit into the second dispersed cell chamber.

It should be noted that the kit instructions would alternately contain instructions on how to complete the cell isolation starting with digestion of a tissue sample as described in the first method embodiment described above.

Advantages of this invention include a simple and rapid method for isolation of cells from tissue. In as little time as 45 minutes, samples of tissue may be taken from a host, digested into component cells, the digested cells separated and applied as seeding cells for use as desired. The device is ideally suited for single use thereby eliminating the need for cleansing and sterilization after use. However, should reuse be desired, the device is easily cleaned and sterilized compared to other known devices as this invention's device does not require any valving which presents a problem for thorough cleaning and sterilization before reuse. Other advantages of this invention include use of the device is possible with minimal instruction, cost and additional equipment.

DETAILED DESCRIPTION OF PREFERRED EMBODIMENTS OF THE INVENTION

Embodiments of the present invention and the advantages thereof are best understood by referring to the following descriptions and drawings, wherein like numerals are used for like and corresponding parts of the drawings.

FIG. 1 is an overall representation of the basic components of an embodiment of the device 100 of this invention.

Device 100 comprises cell isolation unit 200, tissue digestion chamber 300 containing a tissue digestion material 320, waste collection chamber 400, serum chamber 500 containing a serum 510, and dispersed cell chamber 600.

Cell isolation unit 200 comprises a first end 201 and a second end 202. First end 201 optionally contains a removable gauze or filter 210 comprising openings sufficiently large to allow digested cells in the size range of approximately 0.1 to 1000 $\mu$m to pass through while preventing larger undigested tissue from passing through the filter 210. Second end 202 comprises filter 220 which has openings sized to prevent the digested cells from passing through. Typically the openings of filter 220 will range in size from approximately 0.1 to 1000 $\mu$m preferably from 0.4 to 10 $\mu$m. Filters 210 and 220 may be made of any suitable biocompatible material including silk, muslin, stainless steel, fiberglass, cellulose acetate, polyethylene terepthlate, glass, nylon and nitrocellulose. A preferred material for filter 210 is nylon and for filter 220 is nitrocellulose. It is also envisaged that filters 210 and 220 may comprise a series of filters having progressively narrowing apertures that aid in filtering by preventing larger cells or undigested tissue from clogging the finer apertured filters. Also depicted in this embodiment of cell collector 200 is optional channel 230. Channel 230 is a passageway of narrowed diameter compared to first end 201 and second end 202. The purpose of channel 230 is to assist in the separation of digested cells that may be agglomerated before such agglomerates reach filter 220. Channel 230 is also depicted as having transition zone 232 between first end 201 and channel 230 and transition zone 232 between channel 230 and second end 202. For most applications, it is envisaged that the diameter of channel 230 will range from approximately 0.1 mm to 2 mm and the diameters of ends 201 and 202 will range from 1 cm to 10 cm. It should also be noted that although FIG. 1 only depicts one channel 230, it is contemplated that other embodiments of this invention may comprise multiple channels.

In FIG. 1, tissue digestion chamber 300, waste collection chamber 400, serum chamber 500, and dispersed cell chamber 600 are all depicted as tubes having one closed end and one open end. Open end 301 of digestion chamber 300, open end 401 of waste chamber 400, open end 501 of serum chamber 500 and open end 601 of dispersed cell chamber 600 are all adaptably connectable to cell isolation unit 200. Alternately and not shown, chambers 300, 400, 500, and 600 may each comprise syringe type devices each comprising a plunger end and an open end. The open ends of the chambers would be adaptably connectable to open ends 201 and 202 of cell isolation unit 200. In this embodiment, the syringe-type chambers would allow a pressure force to be exerted on the contents of the chambers to force the digested tissue solution to be filtered and digested cells to be collected on filter 220. Likewise, the collected cells would be dispersed by attaching a syringe-type serum chamber 500 which would force the cells to be washed off filter 220 in reverse directed of cells collected.

Cell collector 200, tissue digestion chamber 300, waste chamber 400, serum chamber 500, and dispersed dell chamber 600 may be made of any biocompatible material. Suitable materials include polypropylene, polyethylene, polysulfone, Teflon FEP, Teflon PFA, polystyrene, polycarbonate, stryrene, acrylonitrile, acrylic, glass, and the like.

Operation of the device of the invention may be understood by the reference to FIGS. 2 to 7.

Figure 2:
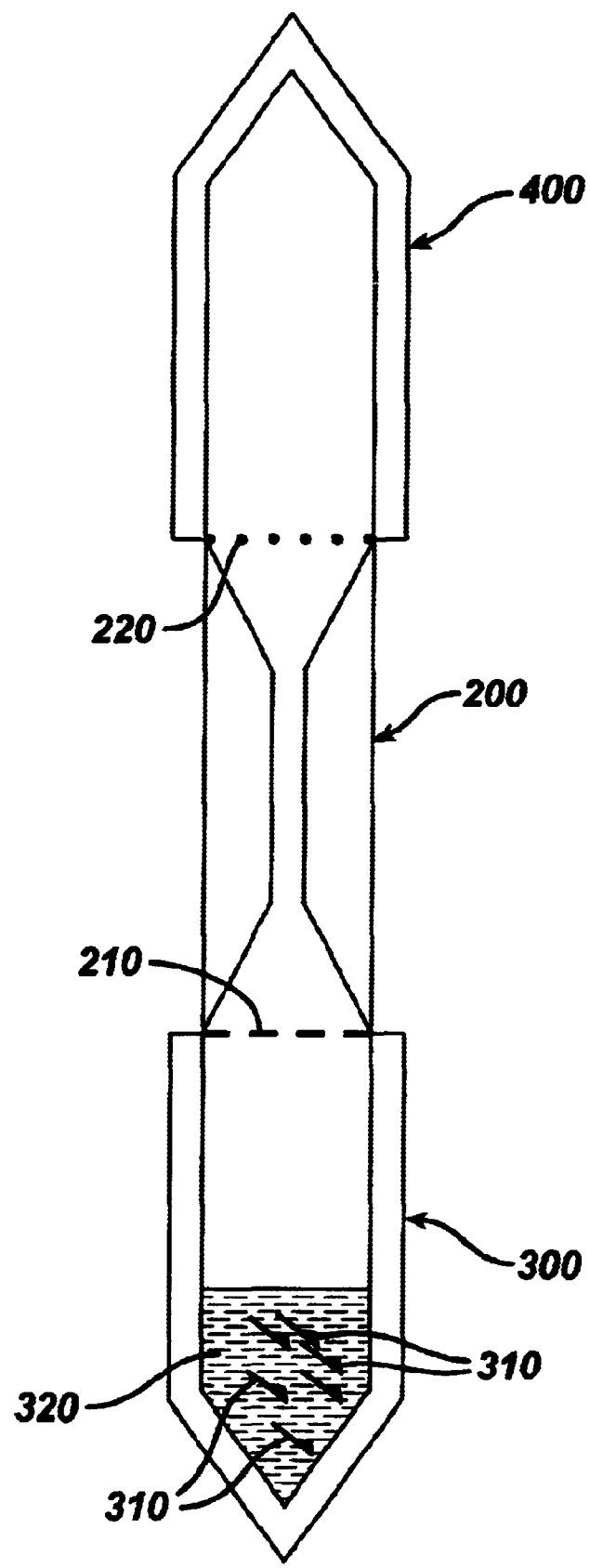
FIG. 2 depicts an embodiment wherein the device of the invention is assembled and awaiting a separation step.

FIG. 2 depicts device 100 assembled prior to application of force (e.g., centrifugal or pressure such as through a syringe type chamber as described above) to cause the digested cells contained in digestion chamber 300 to be separated from the digestion solution and other undigested tissue, if any. Referring to FIG. 2, undigested tissue 310 in shown contained in an acceptable tissue digestion material 320 which digests tissue 310 into isolated cells (not shown). Digestion chamber 300 is releasably connected to cell collector 200 at one end. Waste chamber 400 is connected to cell collector 200 at the end opposite digestion chamber 300.

In preferred embodiments, the host's own tissue 310 is used. Tissue 310 may be taken from the host by conventional means. When the tissue is skin, a preferred way is to remove the tissue by an ultra-thin keratome, which captures the undulating sections of the epidermal/dermal interface. Such a technique allows skin thickness in the vicinity of 0.2 mm to be removed. These ultra-thin slices of tissue aid in the rapid digestion of the tissue to form isolated cells and aid in the rapid healing of the part of the host where the tissue is removed.

Acceptable tissue digestion materials 320 may comprise any suitable solution that will digest the tissue into isolated cells. Suitable materials include enzymes or similar reagents such as proteases, lipases, or hydrolases with ester-hydrolyzing capabilities. Such enzymes include, without limitation, dispase, neuramidase (Sialidase), pancreatin proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase and mixtures thereof. Other suitable enzymes include neutral protease, glycosidase, endopeptidase, pancreatin, metalloprotienase, serine protease, and mixtures thereof. It would be apparent to one skilled to the art that mixtures of the foregoing may be used to effect optimal compositions for digestion of tissue. Preferred enzymes are collagenase and trypsin when the tissue being digested id epidermal skin. Additional agents to increase cell yield and purity such as chelating agents for example ethylenediaminetetraacetic acid (EDTA) or enzymes for nucleic acid digestion deoxyrinonucleicacidase (DNase).

A typical time period to digest a 0.2 mm sample of epidermis skin as the tissue would take approximately 30 minutes at 37° C. using proteases such as collagenase and trypsin. Of course, it will be apparent to one skilled in the art, that digestion time will vary due to such variables as tissue type and thickness and type of and concentration of enzymatic solution being used. Also, enrichment for certain cell types can be obtained from some tissues by the enzymes used and by varying the time of digestion.

Figure 3:
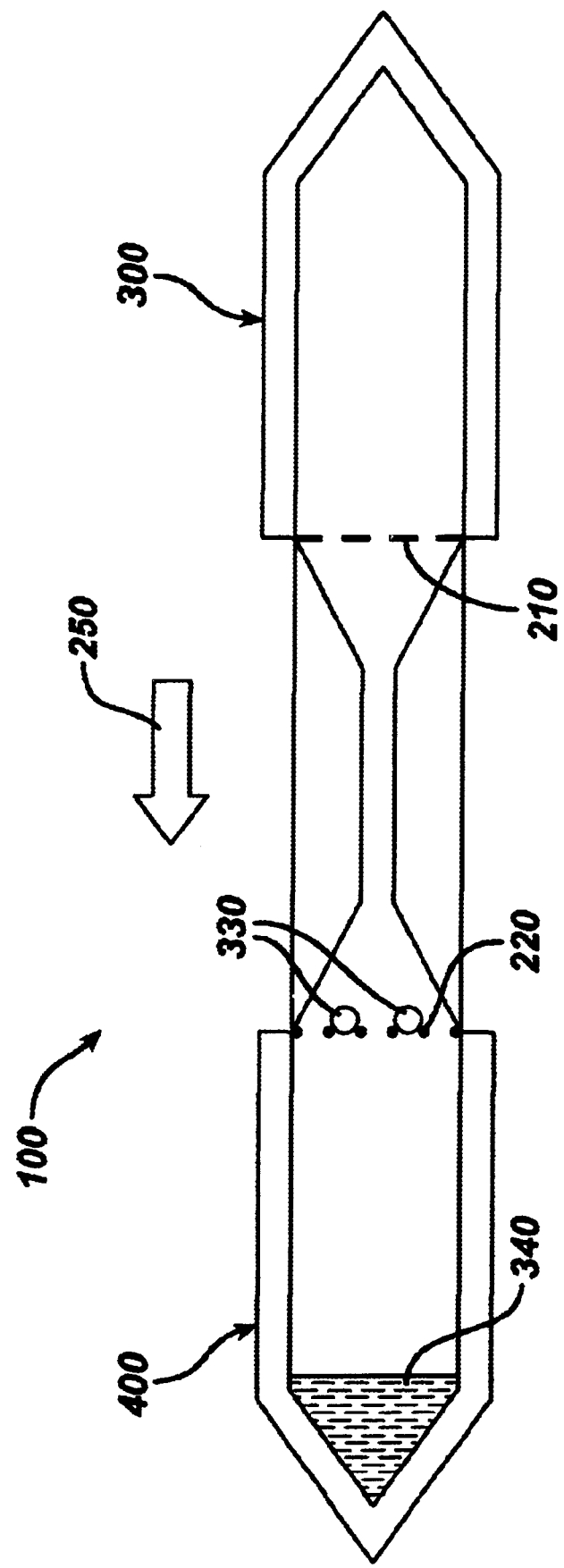
FIG. 3 depicts digested, isolated cells being separated and held on a cell filter.

Once tissue 310 have been sufficiently digested to form a suitable number of isolated cells, the isolated cells are separated from enzymatic solution 320 by the application of force. FIG. 3 depicts the application of centrifugal force as shown by arrow 250 and the aftermath of application of the force. As compared to FIG. 2, FIG. 203 shows that the tissue digestion material 320 and isolated cells 330 have exited digestion chamber 300. Isolated cells 330 accumulate on filter 220. The spent tissue digestion material 340 accumulates in waste chamber 400. Although not shown, filter 210, would accumulate any undigested tissue 310 that was too large to pass through the opening of optional filter 210.

While the above embodiment and following description only discusses centrifugal force to accomplish the separation of cells, it should be appreciated by those skilled in the art that other forms of forces may be included in this invention including but not limited to gravitational force, vacuum, electromagnetic, and centripetal force.

Figure 4A:
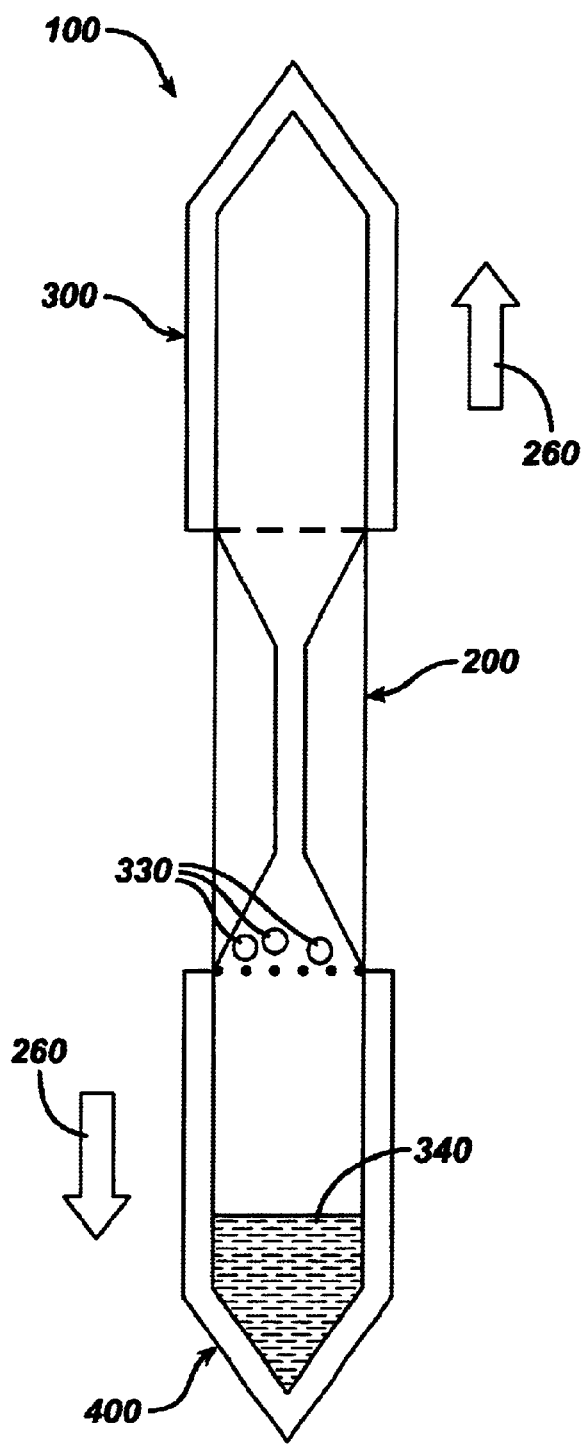
FIG. 4*a* depicts the dismantling of the device after centrifugation.
Figure 4B:
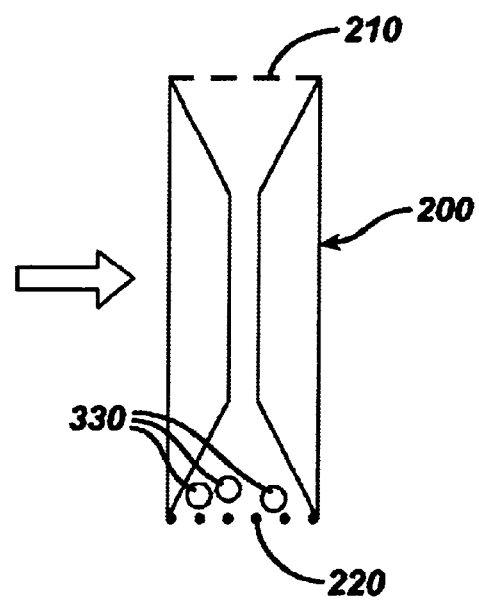
FIG. 4*b* depicts the cell isolation unit with separated cells.

FIGS. 4a and 4b depict the dismantling of device 100 after the application of force to separate isolated cells 330 from the spent enzymatic solution 340. Referring to FIG. 4a, arrows 260 depict the direction that cell digestion chamber 300 and waste chamber 400 are removed from cell isolation unit 200. FIG. 4b depicts the completely disassembled device 100 with cell isolation unit 200 maintaining isolated cells 330 on filter 220. While filer 210 is still depicted, filter 210 is preferably removed prior to the beginning of the next step described below.

Figure 5:
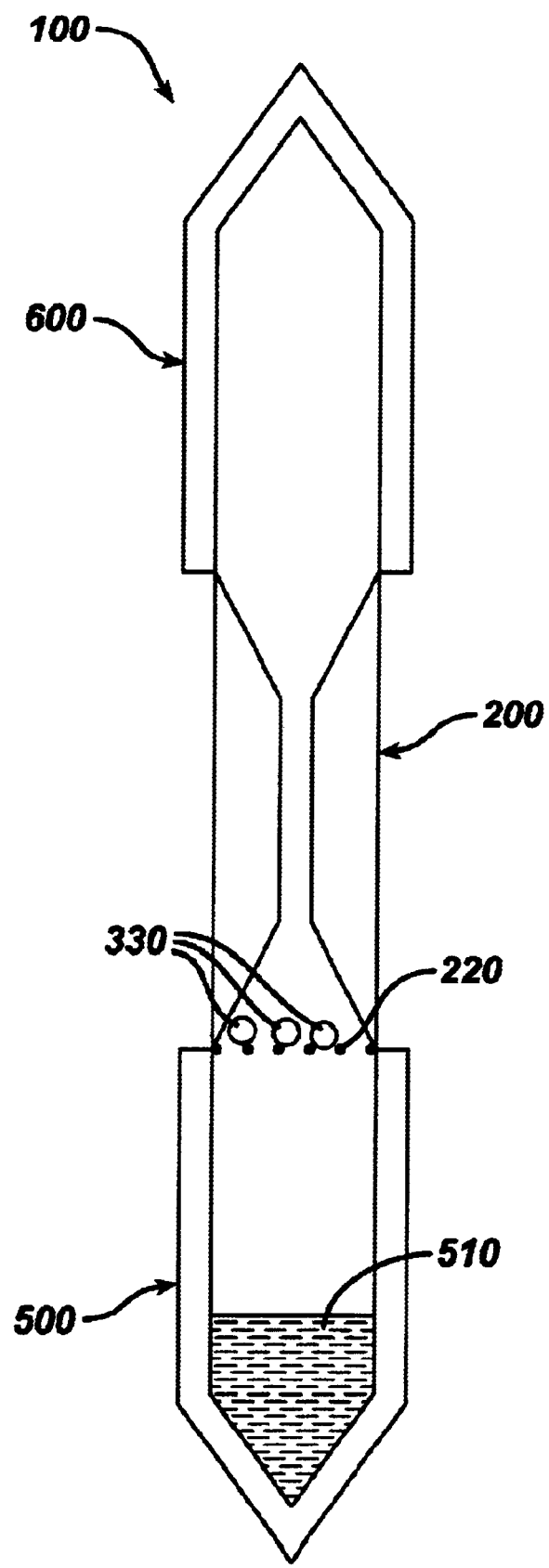
FIG. 5 depicts an embodiment of the invention wherein the separator is assembled prior to washing of the isolated cells into a collection tube.

FIG. 5 depicts device 100 assembled to contain serum chamber 500 and dispersed cell chamber 600. Isolated cells 330 rest on filter 220.

Serum chamber 500 contains any suitable serum 510 capable of dispersing isolated cells 330. Suitable serums include balanced salt solutions, isotonic solutions, cell culture media, buffered salines, whole blood, plasma and mixtures thereof. A preferred serum is isotonic buffered solution of PBS (phosphate buffered saline)

In addition, the serum may contain additional components such as nutrients, growth factors chemotactic factors, cytokines, autocoids, prostanoids, glucocortoids, morphogens, nuclear hormones, receptor agonists and mixtures thereof.

Figure 6:
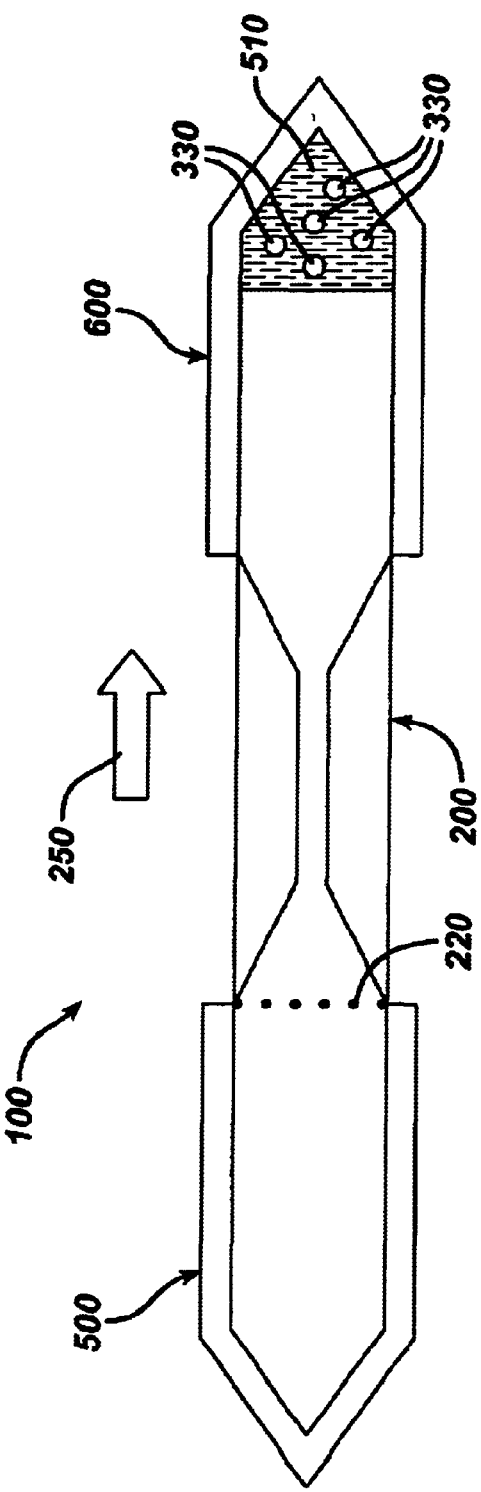
FIG. 6 depicts the centrifugation step wherein the isolated cells are being washed into a collection tube.
Figure 7:
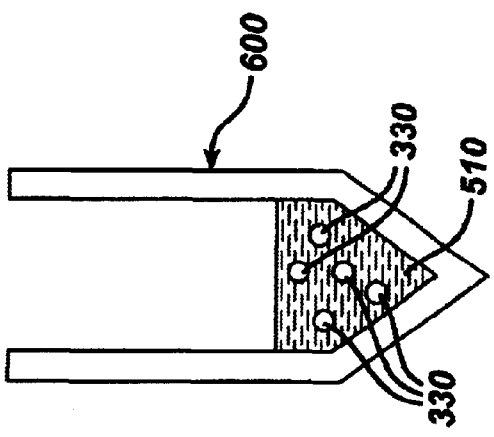
FIG. 7 depicts the collection tube containing isolated cells ready for application.

FIG. 6 depicts the application of centrifugal force to the device as shown in FIG. 5 as shown by arrow 250 and the aftermath of the application of the force. As compared to FIG. 5, FIG. 6 shows that the serum 510 and isolated cells 330 have exited serum chamber 500 and cell isolator 200, respectively. Isolated cells 330 become dispersed in serum 510 in dispersion chamber 600 as shown in FIG. 7.

Figure 8A:
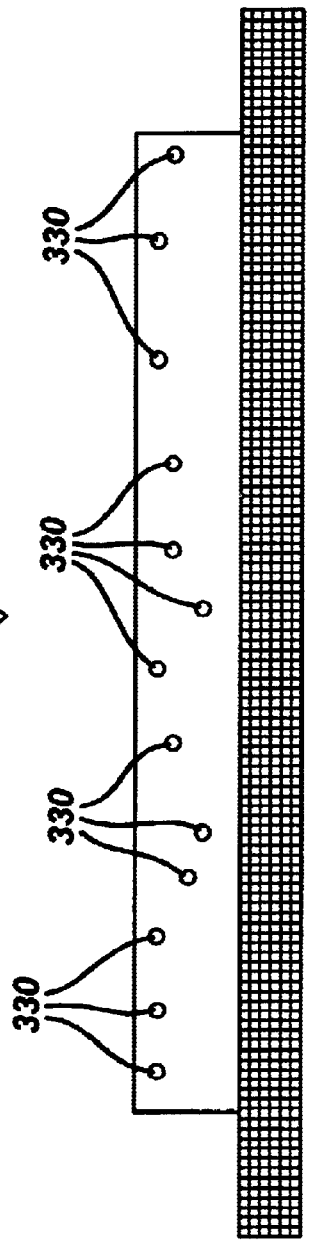
FIG. 8*a* depicts application or seeding of cells to a matrix.
Figure 8B:
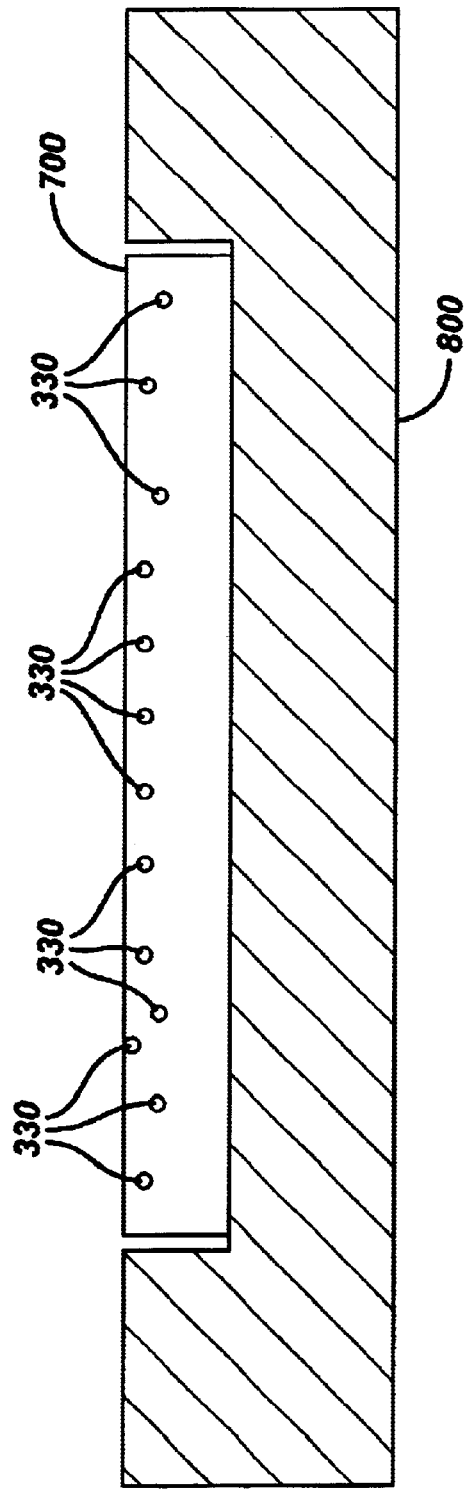
FIG. 8*b* depicts application of the seeded matrix to a wound.

FIGS. 8a and 8b depict a suitable use of the dispersed isolated cells. Referring to FIG. 8a, isolated cells 330 are shown advancing into an extracellular scaffold or matrix 700 via capillary action as depicted by arrow 270 after the content of dispersion chamber 600 had been applied to matrix 700.

Suitable matrices 700 include both biological and synthetic extracellular matrices. Examples of suitable biological extracellular matrices include collagen, fibrin, acellular tissue, coral, alginate, fibronectin, hyaluronic acid and the like. Synthetic extracellular matrices include dextran polymers, polyvinyl chlorides, polyglycolic acids, polylactide acids, polylactic coglycolic acids, silicon, ethylene-vinylacetates, poly-2-hydroxyethyl methacrylate, polytetrafluoroethylene ("PTFE"), poly(ethylene glycol), poly(butylene terepthalate), ceramics and mixtures thereof.

After sufficient time has been allowed for isolation cells 330 to seed matrix 700, the seeded matrix may then be used in a variety of ways.

FIG. 8b depicts one such application of seeded matrix 700 as it is applied to a wound 800.

The device and method of this invention may be used to isolate cells in a sterile manner from various tissues including, but not limited to skin, adipose, muscle, cartilage, liver, pancreas, carotid bodies, omentum and bone. The cells may retain their original phenotype or be stems/progenitor cells that can differentiate into different phenotypes. The isolated cells may be applied to tissue by a variety of methods, used to isolate cells for analysis or cultured in vitro. The isolated cells may be injected directly into tissue, applied to a scaffold of different compositions (protein/polysaccharide/glycosaminoglycan/ceramic), a vehicle of gel, or material to act as a carrier. The cells can be manipulated by genetic engineering or used directly to treat diseases effecting the original organ or other allogenic or autologous tissue. Specific uses are for regeneration or repair of skin, organs, cartilage, bone, skeletal and cardiac muscle or adipose tissue.

EXAMPLE

A sample of epidermis is incubated at 37° C. in the tissue digestion chamber using a protease solution of collagenase and trypsin to dissolve the cell matrix and cell attachment of the tissue sample. The tissue digestion chamber with incubated tissue is attached to the first end of the cell isolation unit with mesh over the opening of the tube to prevent any undigested tissue from entering the cell isolation unit. A waste chamber is attached to the second end of the cell isolation unit with a filter to collect the isolated cells. The assembled device is centrifuged to remove the protease solution from the cells and capture the cells on the filter. The tissue digestion chamber and the waste chamber are removed and a serum chamber containing an isotonic buffered solution of PBS is attached to the second end of the cell isolation unit placed next to the filter. The dispersed cell chamber is attached to the first end of the cell isolation unit. The unit is centrifuged again to wash the cells from the filter with the serum leaving the serum chamber and entering into the cell dispersion chamber. The cells in the serum may be then used in the seeding of a medical device, cultured or cryogenically preserved.

It should be understood that the foregoing disclosure and description of the present invention are illustrative and explanatory thereof and various changes in the size, shape and materials as well as in the description of the preferred embodiment may be made without departing from the spirit of the invention.

| ACTIVITY CODES | |
|---|---|
| Description | Code |
| Preparation of Application | 11 |
| Ordering Patent File History | 12 |
| Validity Search | 21 |
| Patentability Search | 22 |
| Clearance Search/Patent Watch/ Right to Market | 23 |
| Interference-Offense | 31 |
| Interference-Defense | 32 |
| Validity/Infringement Opinion | 41 |
| Initial Filing Fees | 51 |
| Filing Extensions | 52 |
| Other PTO Fees | 53 |
| Prosecution after Filing | 55 |
| Re-examination/Re-issue | 56 |
| Opposition-Offense | 61 |
| Opposition-Defense | 62 |
| Litigation-Offense | 71 |
| Litigation-Defense | 72 |
| Taxes and Annuities | 81 |
| Drawing/Drafting Expenses | 91 |
| Other Disbursements (Travel, Copy, Phone, Postage) | 92 |
| Due diligence (agreements) | 93 |

What is claimed is:

1. A device for separating cells from tissue comprising a housing defining a cell isolation unit having a first end and a second end, a tissue digestion chamber, a dispersed cell chamber, a waste chamber, and a serum chamber, wherein the first end is adaptable for alternately receiving the tissue digestion chamber and the dispersed cell chamber and the second end is adaptable for alternately receiving the waste chamber and the serum chamber and the second end further containing a filter capable of filtering cells from a dispersion.

2. The device of claim 1, wherein the size of the pores of the filter range from 0.1 to 1000 μm.

3. The device of claim 2, wherein the cell isolation unit is in the form of a tube and the chambers are in the form of tubes having one closed end.

4. The device of claim 2, wherein the chambers are syringes adaptably receivable to the ends of the cell isolation unit.

5. The device of claim 3, wherein the tubes are made from a material selected from the group consisting of polypropylene, polyethylene, polysulfone, Teflon FEP, Teflon PFA, polystyrene, polycarbonate, styrene, acrylonitrile, acrylic, glass, and mixtures thereof.

6. The device of claim 3, wherein the cell isolation unit is of varying inner diameter, wherein the diameter at the first end and second end is up to 10 cm and the smaller inner diameter of the cell isolation unit is in the range of 0.1 mm to 2 mm.

7. The device of claim 1 wherein the first end further comprises a filter capable of substantially preventing any undigested tissue from entering the cell isolation unit.

8. The device of claim 7, wherein the size of the pores of the filter at the first end of the cell isolation unit range from 10 to 1000 μm and the pores of the filter at the second end of the cell isolation unit range from 0.4 to 10 μm.

9. A device comprising a housing defining a cell isolation unit having a first end and a second end, a first dispersed cell chamber, a second dispersed cell chamber, a waste chamber, and a serum chamber, wherein the first end is adaptable for alternately receiving the first dispersed cell chamber and the second dispersed cell chamber and the second end is adaptable for alternately receiving the waste chamber and the serum chamber and the second end further containing a filter capable of filtering cells from a dispersion.

10. A method for isolating cells comprising the steps of:
   a) providing a cell isolation unit having first and second open ends;
   b) providing a source of tissue to form cells from tissue digested by a tissue degrading material in a tissue digestion chamber;
   c) providing a waste chamber;
   d) providing a source of serum in a serum chamber;
   e) providing a cell dispersion chamber;
   f) connecting the tissue digestion chamber to the first end of the cell isolation unit and the waste chamber to the second end of the cell isolation unit;
   g) applying a force to cause the cells of the tissue digestion chamber to travel through the cell isolation unit thereby capturing the cells at the second end of the unit and allowing the other contents to pass through the cell isolation unit and into the waste chamber;
   h) disconnecting the tissue digestion chamber and the waste chamber from the cell isolation unit;
   i) connecting the cell dispersion chamber to the first end of the cell isolation unit and the serum chamber to the second end of the cell isolation unit; and
   j) applying a force to cause the contents of the serum chamber to pass through the cell isolation unit thereby washing the cells from the cell isolation unit into the dispersed cell chamber.

11. The method of claim 10, wherein the force described in steps g) and j) is centrifugal force.

12. The methods of claim 10, wherein the tissue degrading material are enzymes.

13. The method of claim 12, wherein the enzymes are selected from the group consisting of dispase, neuramidase (Sialidase), pancreatin proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase, neutral protease, glycosidase, endopeptidase, pancreatin, metalloprotienase, serine protease, and mixtures thereof.

14. The method of claim 13, wherein the enzyme is trypsin.

15. The method of claim 10, wherein the cell digestion chamber and contents of step b) is incubated at temperature near or at 37 C.

16. The method of claim 10, wherein the serum in step d) is selected from the group consisting of balanced salt solutions, isotonic solutions, cell culture mediums, buffered salines and mixtures thereof.

17. The method of claim 16, wherein the serum is phosphate buffered saline.

18. The method of claim 10, further comprising the step of seeding the contents of the cell dispersion chamber of step j) on a matrix suitable for grafting.

19. The method of claim 10, further comprising the step of inserting the contents of the cell dispersion chamber of step j) as a specific cell therapy to assist or augment the functioning of diseased or injured tissue.

20. A method for isolating cells comprising the steps of:
   a) providing a cell isolation unit having first and second open ends;
   b) providing a first dispersion of cells to be separated in a first cell dispersion chamber;
   c) providing a waste chamber;
   d) providing a source of serum in a serum chamber;
   e) providing a second cell dispersion chamber;
   f) connecting the first cell dispersion chamber to the first end of the cell isolation unit and the waste chamber to the second end of the cell isolation unit;
   g) applying a force to cause the cells of the first cell dispersion chamber to travel through the cell isolation unit thereby capturing the cells at the second end of the unit and allowing the other contents to pass through the cell isolation unit and into the waste chamber;
   h) disconnecting the first cell dispersion chamber and the waste chamber from the cell isolation unit;
   i) connecting the second cell dispersion chamber to the first end of the cell isolation unit and the serum chamber to the second end of the cell isolation unit; and
   j) applying a force to cause the contents of the serum chamber to pass through the cell isolation unit thereby washing the cells from the cell isolation unit into the second cell dispersion chamber.

21. A kit for separating cells comprising a housing defining a cell isolation unit having a first end and a second end, a first dispersed cell chamber, a second dispersed cell chamber, a waste chamber, and a serum chamber, wherein the first end is adaptable for alternately receiving the first dispersed cell chamber and the second dispersed cell chamber and the second end is adaptable for alternately receiving the waste chamber and the serum chamber and the second end further containing a filter capable of filtering cells from a dispersion with instructions of use comprising the steps of:

a) providing a first dispersion of cells to be separated in the first dispersed cell chamber;

b) connecting the first dispersed cell chamber to the first end of the cell isolation unit and the waste chamber to the second end of the cell isolation unit;

c) applying a force to cause the cells of the first dispersed cell chamber to travel through the cell isolation unit thereby capturing the cells at the second end of the unit and allowing the other contents to pass through the cell isolation unit and the waste chamber;

d) disconnecting the first dispersed cell chamber and the waste chamber from the cell isolation unit;

e) connecting the second dispersed cell chamber to the first end of the cell isolation unit and the serum chamber containing a serum to the second end of the cell isolation unit; and f) applying a force to cause the contents of the serum chamber to pass through the cell isolation unit thereby washing the cells from the cell isolation unit into the second dispersed cell chamber.

22. A kit for separating cells from tissue comprising a housing defining a cell isolation unit having a first end and a second end, a tissue digestion chamber, a dispersed cell chamber, a waste chamber, and a serum chamber, wherein the first end is adaptable for alternately receiving the tissue digestion chamber and the dispersed cell chamber and the second end is adaptable for alternately receiving the waste chamber and the serum chamber and the second end further containing a filter capable of filtering cells from a dispersion with instructions of use comprising the steps of:

a) providing a source of tissue to form cells from tissue digested by a tissue degrading material in the tissue digestion chamber;

b) connecting the tissue digestion chamber to the first end of the cell isolation unit and the waste chamber to the second end of the cell isolation unit;

c) applying a force to cause the cells of the tissue digestion chamber to travel through the cell isolation unit thereby capturing the cells at the second end of the unit and allowing the other contents to pass through the cell isolation unit and into the waste chamber;

d) disconnecting the tissue digestion chamber and the waste chamber from the cell isolation unit;

e) connecting the cell dispersion chamber to the first end of the cell isolation unit and the serum chamber containing serum to the second end of the cell isolation unit; and f) applying a force to cause the contents of the serum chamber to pass through the cell isolation unit thereby washing the cells from the cell isolation unit into the dispersed cell chamber.

* * * * *

UNITED STATES PATENT AND TRADEMARK OFFICE
CERTIFICATE OF CORRECTION

PATENT NO. : 6,623,959 B2  
DATED : September 23, 2003  
INVENTOR(S) : Ian Ross Harris Page 1 of 1

It is certified that error appears in the above-identified patent and that said Letters Patent is hereby corrected as shown below:

Column 6,  
Line 42, please change "id" to -- is --.

Column 8,  
Line 41, please delete the following:

"

| ACTIVITY CODES | |
|---|---|
| Description | Code |
| Preparation of Application | 11 |
| Ordering Patent File History | 12 |
| Validity Search | 21 |
| Patentability Search | 22 |
| Clearance Search/Patent Watch/ Right to Market | 23 |
| Interference-Offense | 31 |
| Interference-Defense | 32 |
| Validity/Infringement Opinion | 41 |
| Initial Filing Fees | 51 |
| Filing Extensions | 52 |
| Other PTO Fees | 53 |
| Prosecution after Filing | 55 |
| Re-examination/Re-issue | 56 |
| Opposition-Offense | 61 |
| Opposition-Defense | 62 |
| Litigation-Offense | 71 |
| Litigation-Defense | 72 |
| Taxes and Annuities | 81 |
| Drawing/Drafting Expenses | 91 |
| Other Disbursements (Travel, Copy, Phone, Postage) | 92 |
| Due diligence (agreements) | 93 |

"

Signed and Sealed this

Twentieth Day of January, 2004

JON W. DUDAS  
*Acting Director of the United States Patent and Trademark Office*